(12) United States Patent
Liverneaux et al.

(10) Patent No.: US 8,597,363 B2
(45) Date of Patent: Dec. 3, 2013

(54) PROSTHETIC MATERIAL FOR REPLACING AT LEAST ONE PORTION OF THE RADIAL GLENOID OF A RADIUS

(75) Inventors: Philippe Liverneaux, Strasbourg (FR); Jean-Pierre Podgorski, Saint Crespin Sur Moine (FR); Gregoire Larche, Cholet (FR)

(73) Assignee: D.L.P., La Haye Fouassiere (FR)

( * ) Notice: Subject to any disclaimer, the term of this patent is extended or adjusted under 35 U.S.C. 154(b) by 0 days.

(21) Appl. No.: 13/501,202

(22) PCT Filed: Oct. 20, 2010

(86) PCT No.: PCT/FR2010/052236
§ 371 (c)(1),
(2), (4) Date: Apr. 10, 2012

(87) PCT Pub. No.: WO2011/048331
PCT Pub. Date: Apr. 28, 2011

(65) Prior Publication Data
US 2012/0203349 A1 Aug. 9, 2012

(30) Foreign Application Priority Data
Oct. 21, 2009 (FR) .................................... 09 05043

(51) Int. Cl.
*A61F 2/42* (2006.01)
(52) U.S. Cl.
USPC ....................................................... 623/21.12
(58) Field of Classification Search
USPC ....................................................... 623/21.12
See application file for complete search history.

(56) References Cited

U.S. PATENT DOCUMENTS

| | | | |
|---|---|---|---|
| 5,522,902 A * | 6/1996 | Yuan et al. | 623/22.41 |
| 2004/0243241 A1 * | 12/2004 | Istephanous et al. | 623/17.14 |
| 2007/0055381 A1 | 3/2007 | Berelsman et al. | |
| 2008/0103603 A1 * | 5/2008 | Hintermann | 623/20.32 |
| 2009/0254189 A1 * | 10/2009 | Scheker | 623/21.11 |

FOREIGN PATENT DOCUMENTS

| | | |
|---|---|---|
| WO | 2007/047230 A2 | 4/2007 |
| WO | 2007/106358 A2 | 9/2007 |

OTHER PUBLICATIONS

International Search Report for PCT/FR2010/052236, dated Jan. 21, 2011.

* cited by examiner

*Primary Examiner* — Bruce E Snow
*Assistant Examiner* — Melissa Hoban
(74) *Attorney, Agent, or Firm* — Westerman, Hattori, Daniels & Adrian, LLP

(57) ABSTRACT

The prosthetic material for replacing at least one portion of the radial glenoid of a radius includes a plate (2) extended by an endpiece (3) and a set of screws (4) for fastening the plate (2) on the receiving bone material (R). The plate (2) has a planar body (7) extended by an extension (5) forming a portion of the endpiece (3) and having an inner face (5') extending in a general plane (D) that is angularly offset relative to the plane (P) of the plate body (7). This extension (5) co-operates with a fitted panel (6) forming the other portion of the endpiece (3) and having an outer face (3') reproducing at least approximately at least a portion of the surface of the radial glenoid of the radius. The fitted panel is secured on the support extension (5) via a slideway structure (11, 13).

20 Claims, 2 Drawing Sheets

PROSTHETIC MATERIAL FOR REPLACING AT LEAST ONE PORTION OF THE RADIAL GLENOID OF A RADIUS

The present invention relates to prosthetic material for replacing at least one portion of the radial glenoid of a radius.

Some articular pathologies of the distal portion of a radius (lesions of the radial glenoid, in particular traumatic and/or arthritic lesions) may be treated by means of suitable prostheses, which are put into place after cutting bone away and which are held in place by an axial tenon secured to said prosthesis and implanted in the receiving bony material (see in particular documents US-2007/0055381 and WO-2007/047230).

Very generally, some elements of those devices are designed to be fastened to the end of the radius, and other elements are designed to be fastened to the facing bony portions of the hand (carpal bone).

Nevertheless, such prostheses sacrifice firstly a portion of the bony material of the distal radius, and secondly the cartilage of the first carpal row.

Furthermore, in the event of a fracture, this distal portion of the radius is generally repaired by means of screws or pins, possibly associated with a plate fitted on the bone cortex. However, if the fracture is accompanied by lesions in the articular surface of the radius (pre-existing lesions or lesions occurring at the same time as the fracture), then means are not available that are suitable for repairing or reconstructing this articular surface in effective manner.

The present invention proposes prosthetic material for the treatment of damaged articular surfaces of distal portions of the radius, which material is relatively simple to put into place and not very traumatic for the patient.

This prosthetic material also presents the advantage of enabling any fracture(s) present in this bony zone to be reduced.

For this purpose, the prosthetic material in accordance with the invention comprises:

a prosthetic structure constituted by a plate extended by an endpiece, said plate being made up of a planar body extended by a one-piece head, and said plate including a top face and a bottom face, and being provided with through orifices, said plate head itself being extended by said endpiece; and a set of screws for co-operating with said through orifices of said plate to fasten said prosthetic structure to the receiving bony material after resection of the portion of the radial glenoid that it is desired to replace and after positioning the bottom face of said plate against the cortex of said bone material;

and the material is characterized by the fact that said endpiece is constituted by—a support extension made as one piece with said plate head and having an inner face extending in a general plane D that is offset angularly relative to the plane P of said plate body, and by—a fitted articular panel having an outer surface that is situated extending the top face of said plate and reproducing at least approximately at least a portion of the surface of the radial glenoid of the radius, which support extension and fitted panel are provided with means enabling them to be secured to each other, which securing means comprise i) a slideway structure arranged in part on the rear face and/or on the sides of said panel, and also in part on the front face and/or on the sides of said extension, and ii) means for fastening said fitted panel in the correct position on said extension.

Advantageously, the inner face of the support extension extends in a general plane D that is offset at an angle lying in the range 60° to 80° relative to the plane P of the plate body. Furthermore, the plane of movement in translation of the slideway structure preferably lies in a plane parallel to the plane D.

Advantageously, the plate of the prosthetic structure is arranged to be positioned against the anterior cortex of the radius; the structure of the endpiece together with the slideways for positioning the fitted panel make it substantially easier for the practitioner to put the material into place via the operative field which is very generally difficult to access.

Advantageously, the plate extension has two parallel side rails facing each other and suitable for co-operating with two parallel ribs arranged on the sides of said fitted panel.

Furthermore, the means for fastening the panel in the correct position on the extension advantageously comprise abutments formed at one of the ends of the ribs of the fitted panel. These fastener means also preferably comprise locking means of the activatable/deactivatable type that prevent any movement of the fitted panel once it is in place on the plate (these locking means may consist of a screw that is received in a tapped orifice formed in the plate head and having a top end portion that comes into abutment against the top end of the fitted panel).

In a preferred embodiment, at least some of the screws of the plate head are of a length that is adapted for reaching the opposite cortex of the radius so as to enable a bone reduction to be held.

In a preferred embodiment, the width of the endpiece is less than the width of the radial glenoid, said endpiece being arranged to be positioned in a reception zone arranged in the central portion of said radial glenoid, between the radial styloid and the radioulnar joint.

The invention is further illustrated, without any limitation, by the following description of a particular embodiment, given purely by way of example and shown in the accompanying drawings, in which.

The prosthetic material 1 shown in FIGS. 1 to 4 comprises a prosthetic structure 1' made up of a plate 2 that is extended by an endpiece 3 having a front outside face 3' that reproduces a portion of the surface of the radial glenoid of a radius, this assembly being arranged so that said plate 2 can be fastened, by means of screws 4, 4', against the anterior cortex of a radius R, with said endpiece 3 positioned against a reception zone Z corresponding to a deteriorated bony portion that has been resected by a surgeon for the purpose of replacing said bony portion.

Figure 1:
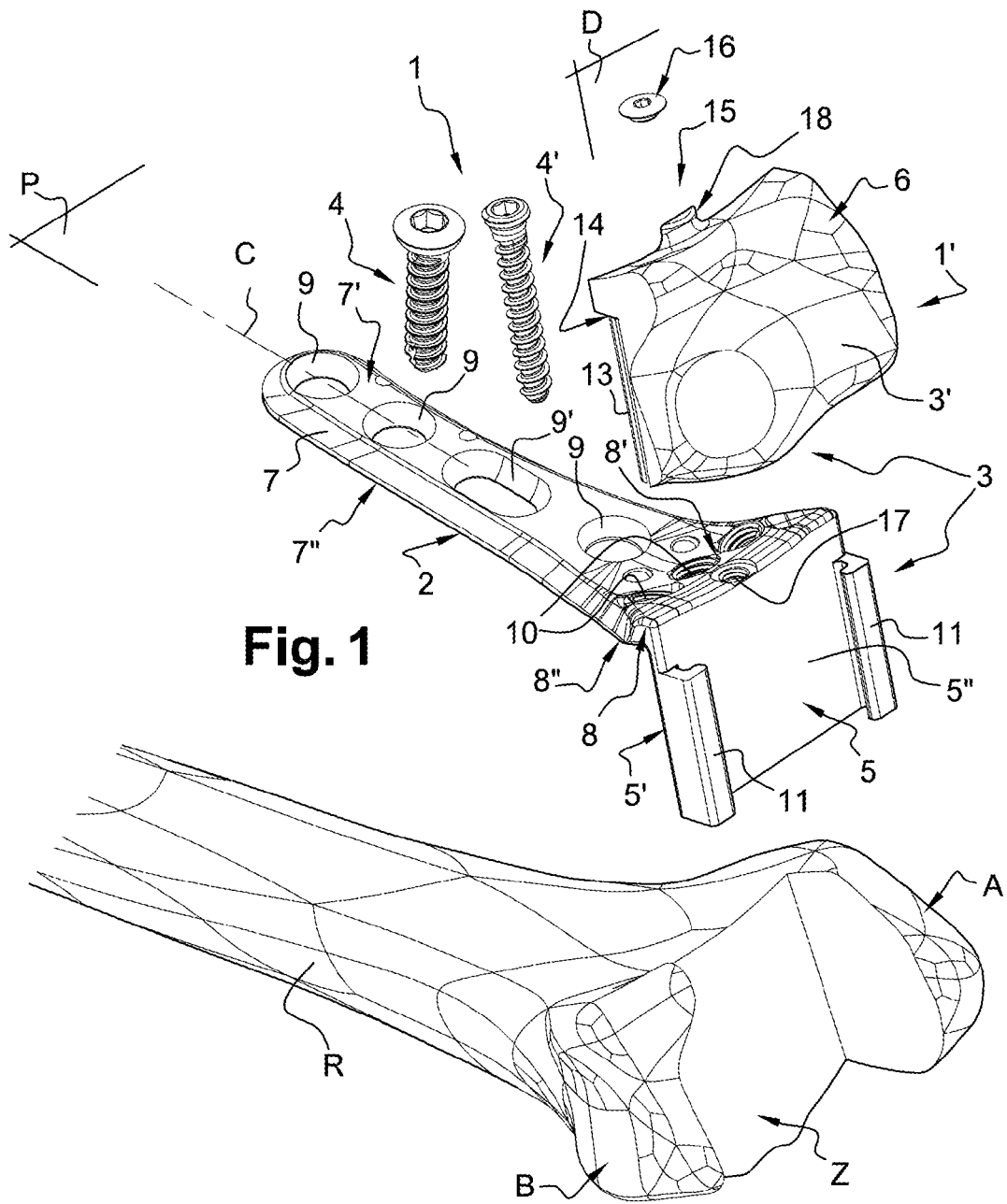
FIG. 1 is a perspective view showing the prosthetic material of the invention, comprising two portions shown separately in this figure (plate and fitted panel), together with some of the fastener screws, that is positioned over a radius that has been suitably prepared for receiving it.
Figure 3:
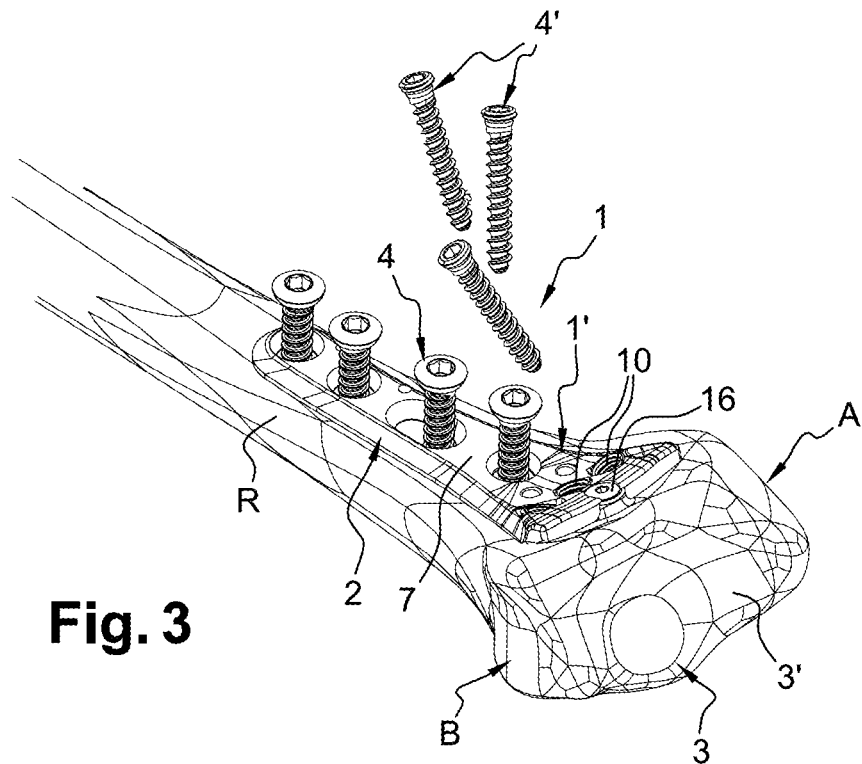
FIG. 3 is a perspective view showing the prosthetic material placed on the distal end of the radius, with some of the fastener screws prepositioned.
Figure 4:
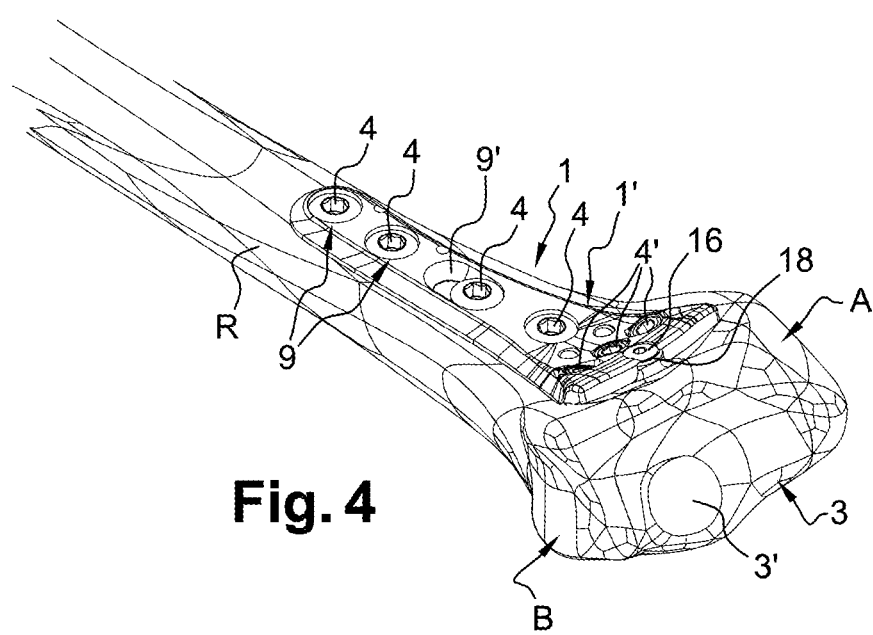
FIG. 4 is a perspective view similar to FIG. 3, with all of the fastener screws put into place.

As can be seen in FIGS. 1, 3, and 4, the reception zone Z may correspond to a reservation arranged in the central portion of the radial glenoid, between the radial styloid A and the radioulnar joint B.

The prosthetic structure 1' in this example is made up of two distinct elements, the first formed by the plate 2 with an extension 5 constituting a portion of the endpiece 3, and the second formed by a panel 6 constituting the other portion of said endpiece 3. As described in greater detail below, this extension 5 and this panel 6 include means enabling them to be secured to each other.

The plate 2 is made up of an elongate body 7 that is extended at one of its ends by a one-piece head 8, itself extended by the above-mentioned one-piece extension 5.

The body 7 and the head 8 of the plate 2 extend practically in the same plane P. They are defined by respective top faces 7' and 8' and respective bottom faces 7" and 8". These bottom faces 7" and 8" match the anatomy at the end of the radius (for which purpose the head 8 rises a little relative to the plane in which the plate body 7 extends).

The plate body 7 is pierced by a plurality of orifices 9, 9' in alignment on its axis C. One of these orifices 9' is generally oblong in shape; it is preferably located in the central portion of the plate body 7. The other orifices 9, arranged on either side of the oblong orifice 9', are generally circular in shape. The orifices 9 and 9' are designed to receive fastener screws 4, only one of which is shown in FIG. 1.

The plate head 8 is also pierced by a plurality of orifices 10 (three in this example, arranged in alignment across its width, i.e. transversely relative to the axis C of the plate body 7). These orifices 10 are designed to receive screws 4' (only one of which is shown in FIG. 1) that are adapted in particular for holding a bone fracture reduction.

The extension 5 extends beside the bottom face 7", 8" of the plate body 7 and of the plate head 8, going from the end of said plate head 8, with this taking place in a plane D that is angularly offset relative to the plane P of the plate body 7. The corresponding angular offset in this example is about 75°.

This extension 5 consists in a slab having a rear face 5' that is placed beside the bottom faces 7" and 8" of the body 7 and the head 8 of the plate 2, and having a front face 5" that extends the top faces 7' and 8' of said plate body and head 7 and 8. The rear and front faces 5' and 5" of the extension 5 are parallel and they both extend in the plane D. The front face 5" of the extension 5 includes means enabling it to receive and fasten the endpiece 3, these means being in the form of two parallel rails 11 that face each other. These two rails 11 extend parallel to the plane D of the extension 5 and along the side margins thereof.

The plate 2 may be made of a metal, such as titanium, for example.

Figure 2:
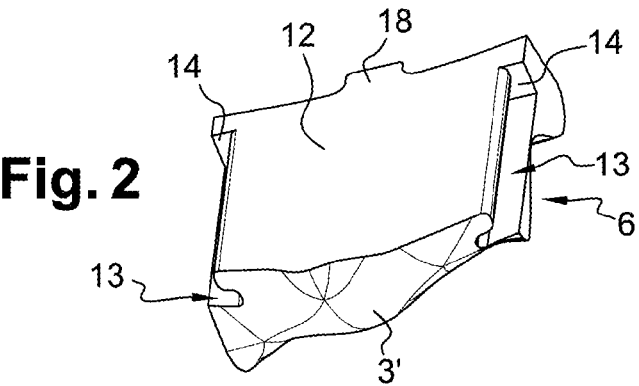
FIG. 2 is a perspective view of the fitted panel, shown with its rear face visible.

The panel 6, shown on its own in FIG. 2, has a front face 3' that constitutes the front face of the endpiece 3 and that reproduces, at least approximately, the surface portion of the radial glenoid of the radius. Its rear face 12 is adapted to be secured to the front face 5" of the extension 5 of the plate 2. For this purpose, the rear face 12 of the panel 6 is plane and on its side it includes two parallel ribs 13 suitable for being slidably inserted in the rails 11 of the extension 5.

The ribs 13 of the panel 6 and the rails 11 of the extension 5 thus form a slideway structure enabling the panel 6 to be mounted on the end of the plate 2 along an axis (or a plane) that is parallel to the plane D, in this example.

In the top portion of the ribs 13, there can be seen abutments 14 that serve to block the advance of the panel 6 over the extension 5, by coming into contact with the top ends of the rails 11. The panel 6 is positioned on the plate 2 from above the rails 11 (i.e. from the same side as the top faces 7' and 8' of the plate body 7 and the plate head 8). The abutments 14 thus block further downward advance of the panel 6, assuming the elements are oriented as shown in FIG. 1.

Anti-return means 15 of activatable/deactivatable type are provided to lock the panel 6 completely once it has been properly positioned on the plate 2. In this example, these locking means 15 are provided at the end of the plate head 8; they comprise a screw 16 suitable for being received in a tapped orifice 17 formed in the plate head 8, with a top end portion of the screw (screw head) being arranged to come into abutment against the top margin of the fitted panel 6. Specifically, the screw 16 comes into abutment against a lug 18 that projects a little from the top margin of the panel 6, thus acting in combination with the abutment 14 to prevent any possibility of said panel 6 moving once it is in position.

Once the panel 6 has been fastened to the extension 5, its plane rear face 12 faces the plane front face 5" of the extension 5, in contact therewith, or practically in contact therewith.

The endpiece 3 as formed in this way has an outer front face 3' reconstituting the surface of the resected radial glenoid, and an inner face 5' corresponding to the rear face of the extension 5 and extending in the plane D.

The panel 6 may be made of any biocompatible material, for example chromium-cobalt, PEEK (polyetheretherketone), polyethylene, or pyrolithic carbon.

In association with the plate 2, it is preferable to provide a set of panels 6 of different thicknesses that are made available to the surgeon, so as to offer him a choice of prostheses as a function of the depth of the resection that he has needed to perform in the bone.

The prosthetic material of the invention finds a particularly advantageous application in the event of a fracture of the distal end of the radius that is accompanied by lesions of the articular surface (on the radial glenoid).

The surgeon may then advantageously make use of an operating technique with an approach from the palm side.

For that purpose, after opening the patient's skin at the wrist, the practitioner resects the damaged radial glenoid, and manually reduces the bone fracture. Thereafter, the plate 2 is appropriately positioned on the anterior cortex of the radius, together with the extension 5 and the associated panel 6 in the reception zone Z (FIG. 3), prior to closing the operative field.

More precisely, the plate 2 may initially be prepositioned on the radius without the panel 6, merely making use of a central screw 4 received in the oblong orifice 9'. By tracking with an image intensifier, this enables the surgeon to test different panels 6, to adjust the position of the plate 2 on the radius, and to reduce the fracture temporarily by using pins.

When the positioning for the plate 2 has been decided, the surgeon fastens it appropriately by means of screws 4 in the orifices 9 of the plate body 7 and by means of screws 4' in the orifices 10 of the plate head 8 (FIGS. 3 and 4). As mentioned above, these are arranged so as to hold the bone fracture reduction. In this context, they are of a length that is suitable for reaching the opposite cortex of the radius; these screws 4' may be locked to the plate 2 by means of a poly-axial locking system. The surgeon may then terminate the operation by performing the ligament balance, and then by positioning the final plate 6 on the plate extension 5, prior to closing the operative field.

In a variant embodiment, the plate 2 may be made as a plurality of portions that are provided with means for being assembled together.

The invention claimed is:

1. Prosthetic material for replacing at least one portion of the surface of the radial glenoid of a radius, which material comprises:
   a prosthetic structure constituted by a plate extended by an endpiece, said plate being made up of a planar plate body located in a main plane, extended by a one-piece plate head, and said plate including a top face and a bottom face, and being provided with through orifices, said plate head itself being extended by said endpiece, wherein a bottom face of the plate head rises upwardly from the plate body toward the endpiece; and a set of screws for co-operating with said through orifices of said plate to fasten said prosthetic structure to a receiving bony material after resection of the portion of the radial glenoid that it is desired to replace and after positioning the bottom face of said plate against a cortex of said receiving bony material;

wherein said endpiece comprises:

a support extension made as one piece with said plate head and having an inner face extending downwardly from the plate head in a general plane that is offset angularly relative to the main plane of said plate body at an angle lying in the range 60° to 80° relative to the main plane of the plate body, said support extension having a front face opposed to said inner face, and a fitted articular panel having an outer surface that is situated extending the top face of said plate in the tangential continuity of said top face, and reproducing at least approximately at least a portion of the surface of the radial glenoid of the radius, said fitted articular panel having a rear face opposed to said outer surface, wherein the support extension and the fitted articular panel are provided with means enabling them to be secured to each other, which securing means comprise i) a slideway structure arranged in part on at least one of (a) the rear face and (b) sides of said fitted articular panel, and also in part on at least one of (a) the front face and (b) sides of said support extension, and ii) means for fastening said fitted articular panel in a correct position on said support extension, wherein in the correct position, the rear face of the fitted articular panel faces the front face of the support extension.

2. Material according to claim 1, wherein a plane of movement in translation of the slideway structure lies in a plane parallel to said general plane.

3. Material according to claim 2, wherein the support extension has two parallel side rails facing each other and two parallel ribs are arranged on the sides of the fitted articular panel, the side rails of said plate extension being suitable for co-operating with two the parallel ribs arranged on the sides of said fitted articular panel.

4. Material according to claim 3, wherein said means for fastening the fitted articular panel in the correct position on the extension comprise abutments formed at one of the ends of the ribs of said fitted articular panel.

5. Material according to claim 4, wherein
the slideway structure is oriented so that the fitted articular panel slides downwardly on the support extension from a top side of the support extension until the fitted articular panel reaches the correct position in abutment against the support extension, and
the means for fastening the fitted articular panel in the correct position on the support extension comprises activatable and deactivatable locking means that prevent any movement of the fitted panel once it is in place on the plate, wherein said locking means comprise a screw that is received in a tapped orifice formed in a top face of the plate head, said screw having a top end portion that comes into abutment against a top end of the fitted panel so as to prevent it from sliding upwardly.

6. Material according to claim 2, wherein said means for fastening the fitted articular panel in the correct position on the extension comprise activatable and deactivatable locking means that prevent any movement of the fitted articular panel once it is in place on the plate.

7. Material according to claim 6, wherein said locking means comprise a screw that is received in a tapped orifice formed in the plate head and having a top end portion that comes into abutment against a top end of the fitted articular panel.

8. Material according to claim 2, wherein
the slideway structure is oriented so that the fitted articular panel slides downwardly on the support extension from a top side of the support extension until the fitted articular panel reaches the correct position in abutment against the support extension, and
the means for fastening the fitted articular panel in the correct position on the support extension comprises activatable and deactivatable locking means that prevent any movement of the fitted panel once it is in place on the plate, wherein said locking means comprise a screw that is received in a tapped orifice formed in a top face of the plate head, said screw having a top end portion that comes into abutment against a top end of the fitted panel so as to prevent it from sliding upwardly.

9. Material according to claim 1, wherein the support extension has two parallel side rails facing each other and two parallel ribs are arranged on the sides of the fitted articular panel, the side rails of said support extension being suitable for co-operating with the parallel ribs of said fitted articular panel, so as to form the slideway structure.

10. Material according to claim 9, wherein said means for fastening the fitted articular panel in the correct position on the support extension comprise abutments formed at one of the ends of the ribs of said fitted articular panel.

11. Material according to claim 10, wherein said means for fastening the panel in the correct position on the extension comprise activatable and deactivatable locking means type that prevent any movement of the fitted panel once it is in place on the plate.

12. Material according to claim 11, wherein said locking means comprise a screw that is received in a tapped orifice formed in the plate head and having a top end portion that comes into abutment against a top end of the fitted articular panel.

13. Material according to claim 9, wherein said means for fastening the fitted articular panel in the correct position on the extension comprise activatable and deactivatable locking means that prevent any movement of the fitted articular panel once it is in place on the plate.

14. Material according to claim 13, wherein said locking means comprise a screw that is received in a tapped orifice formed in the plate head and having a top end portion that comes into abutment against a top end of the fitted articular panel.

15. Material according to claim 1, wherein the plate of the prosthetic structure is arranged to be positioned against the anterior cortex of the radius.

16. Material according to claim 1, wherein at least some of the screws of the plate head are of a length that is adapted for reaching the opposite cortex of the radius so as to enable a bone reduction to be held.

17. Material according to claim 1, wherein the width of the endpiece is less than the width of the radial glenoid, and said endpiece is arranged to be positioned in a reception zone arranged in the central portion of said radial glenoid, between the radial styloid and the radioulnar joint.

18. Material according to claim 1, wherein said means for fastening the fitted articular panel in the correct position on the extension comprise activatable and deactivatable locking means that prevent any movement of the fitted articular panel once it is in place on the plate.

19. Material according to claim 18, wherein said locking means comprise a screw that is received in a tapped orifice formed in the plate head and having a top end portion that comes into abutment against a top end of the fitted articular panel.

20. Material according to claim 1, wherein
the slideway structure is oriented so that the fitted articular panel slides downwardly on the support extension from a top side of the support extension until the fitted articular panel reaches the correct position in abutment against the support extension, and
the means for fastening the fitted articular panel in the correct position on the support extension comprises activatable and deactivatable locking means that prevent any movement of the fitted panel once it is in place on the plate, wherein said locking means comprise a screw that is received in a tapped orifice formed in a top face of the plate head, said screw having a top end portion that comes into abutment against a top end of the fitted panel so as to prevent it from sliding upwardly.

\* \* \* \* \*